(12) United States Patent
Bigot et al.

(10) Patent No.: US 8,207,355 B2
(45) Date of Patent: Jun. 26, 2012

(54) METHOD FOR PREPARING AZETIDINE DERIVATIVES

(75) Inventors: Antony Bigot, Paris (FR); Philippe Boffelli, Paris (FR); Maxime Lampilas, Paris (FR); Pascale Marolleau, Paris (FR); Alain Medard, Paris (FR); Gilles Oddon, Paris (FR); Daniel Varraillon, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/814,994

(22) Filed: Jun. 14, 2010

(65) Prior Publication Data

US 2011/0118481 A1    May 19, 2011

Related U.S. Application Data

(63) Continuation of application No. PCT/FR2008/001728, filed on Dec. 12, 2008.

(30) Foreign Application Priority Data

Dec. 14, 2007 (FR) .................................... 07 08746

(51) Int. Cl.
*C07D 205/04* (2006.01)
(52) U.S. Cl. ....................................................... 548/953
(58) Field of Classification Search ........................ None
See application file for complete search history.

(56) References Cited

U.S. PATENT DOCUMENTS 6,355,631 B1   3/2002   Achard et al.

FOREIGN PATENT DOCUMENTS

| EP | 0863136 | 9/1998 |
| WO | WO01/64634 | 9/2001 |
| WO | WO2006/040464 | * 10/2005 |
| WO | WO2007/064566 | 6/2007 |

OTHER PUBLICATIONS

Sammes, P.G. et al., "On the Synthesis of Zaetidines from 3 Hydroxypropylamines," Journal of the Chemical Society, Chemical Communications, Chemical Society, Letchworth, GB, Jan. 1, 1983, pp. 682.
Edmondson, Scott D. et al., "(25,3S)-3-Amino-4-(3,3-difluoropyrrolidin- 1 -yl)-N,N-dimethy1-4-oxo-2-(4- [1,2,4]triazolo[1,5-a]-pyridin-6-ylphenyl)butanamide: A Selective a-Amino Amide Dipeptidyl Peptidase IV Inhibitor for the Treatment of Type 2 Diabetes," Journal of Medicinal Chemistry (2006), vol. 49, pp. 3614-3627.
International Search Report dated Jul. 1, 2009 issued in PCT/FR2008/001728.

* cited by examiner

*Primary Examiner* — Sun Jae Loewe
(74) *Attorney, Agent, or Firm* — Scully, Scott, Murphy & Presser P.C.

(57) ABSTRACT

This invention discloses and claims an industrial method for the production of azetidine derivatives, such as, N-(1-benzhydrylazetidin-3-yl)-N-phenylmethylsulphonamide.

19 Claims, No Drawings

METHOD FOR PREPARING AZETIDINE DERIVATIVES

The present invention relates to a process for preparing azetidine derivatives, such as, N-(1-benzhydrylazetidin-3-yl)-N-phenylmethylsulphonamide of formula (I):
in which:

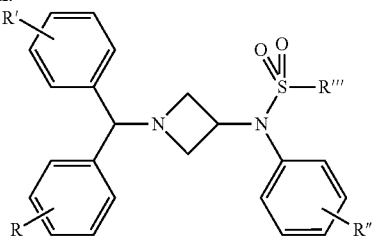

R, R' and R" represent, independently of one another, one or more hydrogen, halogen (Cl, F, Br, I), cyano or nitro radicals, linear or branched alkyl radicals containing from 1 to 6 carbon atoms, linear or branched alkoxy radicals containing from 1 to 6 carbon atoms, linear or branched alkyl carboxylate radicals, wherein the alkyl group contains from 1 to 6 carbon atoms, or trifluoromethyl or trifluoromethoxy radicals;

R''' represents a linear or branched alkyl or perfluoroalkyl group containing from 1 to 6 carbon atoms or an aryl group optionally substituted with one or more R" radicals.

The process for synthesizing the compounds of formula (I) according to the present invention is characterized in that it comprises the following steps:

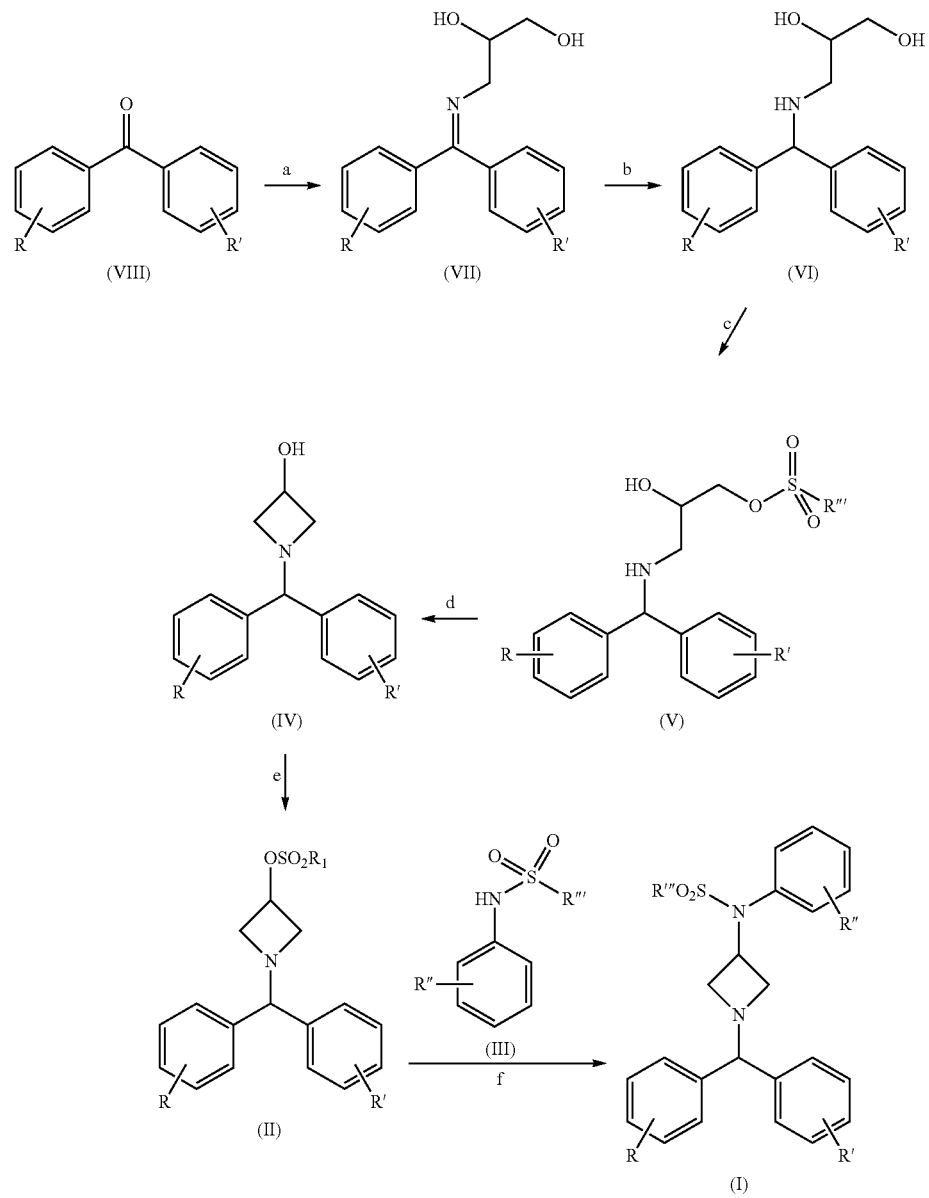

a) a ketone of formula (VIII) is condensed with 3-amino-1, 2-propanediol, in the presence or absence of a solvent, in the presence or absence of an acidic or basic catalyst, at a temperature of between 0° C. and 150° C.;

b) the imine diol of formula (VII) obtained in step a), and optionally not isolated, is reduced with a borohydride or hydrogen gas, in the presence of a metal catalyst in a solvent so as to form the amine diol of formula (VI);

c) the amine diol of formula (VI) obtained in step b), and optionally not isolated, is activated with a sulphonylating agent in the presence of a base, in a solvent and, optionally, a cosolvent at a temperature ranging from −78° C. to 40° so as to form a sulphonic ester of formula (V), optionally not isolated;

d) the sulphonic ester of formula (V) obtained in step c), and optionally not isolated, is cyclized by heating in a solvent in the presence or absence of a base, between 0° C. and 130° C., so as to form the azetidinol of formula (IV), and is optionally isolated in the form of a salt;

e) the azetidinol of formula (IV) obtained in step d) is converted to the sulphonate of formula (II) through the action of a sulphonylating agent in the presence of a base, in a solvent, at a temperature of between −78° and +40° C.;

f) the sulphonate obtained in step e) is condensed with a sulphonamide of formula (III) in the presence of a base, in the same solvent as that used in step e), so as to form the compound of formula (I).

In formulae (I), (II), (III), (IV), (V), (VI), (VII) and (VIII), R, R' and R'' represent, independently of one another, one or more hydrogen, halogen (Cl, F, Br, I), cyano or nitro radicals, linear or branched alkyl radicals containing from 1 to 6 carbon atoms, linear or branched alkoxy radicals containing from 1 to 6 carbon atoms, linear or branched alkyl carboxylate radicals, wherein the alkyl group contains from 1 to 6 carbon atoms, or trifluoromethyl or trifluoromethoxy radicals; R''' represents a linear or branched alkyl or perfluoroalkyl group containing from 1 to 6 carbon atoms or an aryl group optionally substituted with one or more R'' radicals; and R1 represents a methyl group, $CF_3$ group, $C_4F_9$ group, $C_8F_{17}$ group or phenyl group optionally substituted with a methyl, halo or nitro group.

Document WO 01/64634 describes general routes of access for obtaining such products, and in particular the synthesis of the azetidinols of formula (IV) from the amino derivative and epichlorohydrin or epibromohydrin in an inert solvent. On an industrial scale, the use of such reactants may present health risks for those who handle them, and becomes very restrictive; furthermore, the quantification of residual traces thereof is extremely low. Consequently, the setting up of an alternative process that no longer uses this type of reactant becomes important. The present invention makes it possible to do away with the use of such reactants while maintaining an efficiency for large-scale production.

Patent application WO 01/64634 describes general routes of access for obtaining products of formula (I), and in particular a synthesis by condensation of a sulphonate and of a sulphonamide, in an inert solvent such as dioxane, in the presence of $Cs_2CO_3$ at the reflux temperature of the reaction mixture. The operating conditions for the synthesis of compounds of formula (I) as they are described in document WO 01/64634 cannot be transposed to an industrial scale, either in terms of industrial hygiene and safety for handlers, or in terms of residual traces of reactants such as $Cs_2CO_3$ and dioxane. This new process provides significant improvements in terms of safety, and also a simplification of the synthesis steps by using a single solvent in the two steps. The steps of purification and isolation of intermediates and of the final product, by silica chromatography, have been eliminated and replaced with crystallizations, in order to make the process compatible with industrial production.

Steps e) and f) are carried out in the same solvent and without any phase-transfer agent. The synthesis conditions must be compatible with a large-scale production and the residual traces of solvents must be of no consequence. Furthermore, it has been found that the use of the same solvent in steps e) and f) is possible.

The operation is carried out in a solvent compatible with the constraints of the two steps, and it has been found, surprisingly, that a solvent of ketone type, such as methyl isobutyl ketone or methyl ethyl ketone, is compatible.

The compound of formula (I) is obtained after condensation of the sulphonate of formula (II) with a sulphonamide of formula (III), in which R, R', R'', R''' and R1 are as defined above. The formation of the compound of formula (I) is carried out by addition of sulphonamide of formula (III) to the sulphonate of formula (II) in (III)/(II) molar proportions of 1 to 1.3 in the presence of a base, for example potassium carbonate, in a solvent such as methyl ethyl ketone or methyl isobutyl ketone at a temperature of between 80° C. and 118° C. It has also been found that the absence of catalyst in this condensation step promotes the reduction in impurities.

The sulphonate of formula (II), in which R1 is as defined above, is obtained from the azetidinol of formula (IV), in which R and R' are as defined above, after reaction with a sulphonylating agent. This reaction is carried out in the presence of a base such as triethylamine (TEA), diisopropylethylamine (DIPEA), 1,5-diazabicyclo[4.3.0]non-5-ene (DBN) or 1,8-diazabicyclo[5.4.0]undec-7-ene (DBU). The reaction is carried out at between −78° C. and +40° C.

The sulphonamide of formula (III), in which R'' and R''' are as defined above, is obtained from 3,5-difluoroaniline, in the presence of a solvent such as THF (tetrahydrofuran) or a ketone such as MiBuK (methyl isobutyl ketone) or MEK (methyl ethyl ketone) and of a base such as triethylamine (TEA), diisopropylethylamine (DIPEA), 1,5-diazabicyclo[4.3.0]non-5-ene (DBN) or 1,8-diazabicyclo[5.4.0]undec-7-ene (DBU).

The azetidinol of formula (IV), in which R and R' are as defined above, is obtained from the sulphonic ester derivative, optionally not isolated, of formula (V), in which R and R' represent, independently of one another, one or more hydrogen, halogen (Cl, F, Br, I), cyano or nitro radicals, linear or branched alkyl radicals containing from 1 to 6 carbon atoms, linear or branched alkoxy radicals containing from 1 to 6 carbon atoms, linear or branched alkyl carboxylate radicals, wherein the alkyl group contains from 1 to 6 carbon atoms, or trifluoromethyl or trifluoromethoxy radicals, and R''' represents a linear or branched alkyl or perfluoroalkyl group containing from 1 to 6 carbon atoms or an aryl group optionally substituted with one or more R'' radicals.

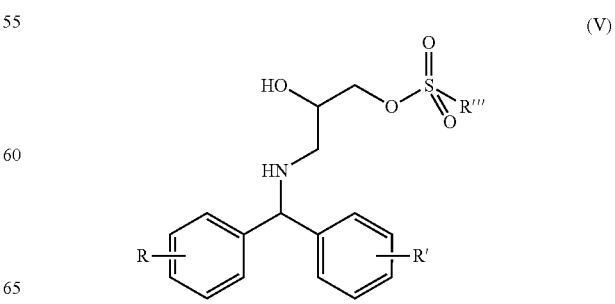

(V)

The azetidinol of formula (IV) is formed by heating the sulphonic ester of formula (V) in a solvent, in the presence or absence of a base, and at a temperature of between 0° and 130° C., for example between 40° C. and 110° C.

The term "solvents" is intended to mean aromatic solvents such as toluene, xylene or chlorobenzene, ethers such as THF (tetrahydrofuran), DME (dimethoxyethane), MTBE (methyl tert-butyl ether) or dioxane, chlorinated solvents such as dichloromethane, chloroform or 1,2-dichloroethane, esters such as ethyl acetate or butyl acetate, nitriles such as acetonitrile, ketones such as acetone, methyl ethyl ketone or methyl isobutyl ketone, amides such as DMF (dimethylformamide), DMAC (dimethylacetamide) or NMP(N-methylpyrrolidone), and alcohols such as methanol, ethanol, isopropanol or butanol.

The term "base" is intended to mean amines (triethylamine, diisopropylethylamine, etc.), hydrogen carbonates, carbonates, hydroxides or phosphates of alkali metals such as lithium, sodium, potassium or caesium.

Another embodiment consists in carrying out the operation in toluene under hot conditions at 80° C. in the presence of an inorganic base, in particular NaHCO$_3$ (sodium hydrogen carbonate) or Na$_2$CO$_3$ (sodium carbonate).

The derivative of formula (IV) may be isolated, purified in the form of an HX salt, X being a Cl, Br or BF$_4$.

The derivative of formula (V), in which R and R' are as defined above, is synthesized from an amine diol of formula (VI), in which R and R' represent, independently of one another, one or more hydrogen, halogen (Cl, F, Br, I), cyano or nitro radicals, linear or branched alkyl radicals containing from 1 to 6 carbon atoms, linear or branched alkoxy radicals containing from 1 to 6 carbon atoms, linear or branched alkyl carboxylate radicals, wherein the alkyl contains from 1 to 6 carbon atoms, or trifluoromethyl or trifluoromethoxy radicals.

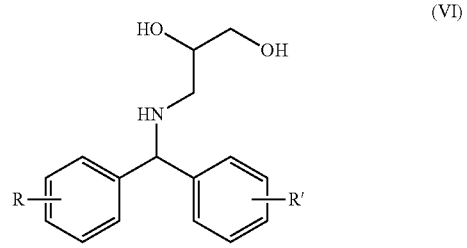

(VI)

The sulphonic ester of formula (V) is formed by adding a sulphonylating agent to the amine diol (VI), in the presence of a base, in a solvent and at a temperature of between −78° C. and +40° C., for example between −30° C. and 20° C. It is also possible to add a catalytic amount (from 1 to 100 mol % relative to the amine of formula (VI)) of a substituted pyridine such as 4-N,N-dimethylaminopyridine (DMAP).

The term "sulphonylating agent" is intended to mean alkyl (methyl, ethyl, trifluoromethyl, etc.) or aryl (phenyl, paramethylphenyl, etc.) sulphonyl halides (fluorides, chlorides, bromides) or else the corresponding sulphonic anhydrides. The sulphonylating agent is used in proportions ranging from 1 to 3.5 equivalents relative to the amine diol (VI).

The term "base" is intended to mean amines (triethylamine, diisopropylethylamine, etc.), pyridine (unsubstituted or substituted with alkyl groups), hydrogen carbonates, carbonates, hydroxides or phosphates of lithium, sodium, potassium or caesium alkali metals.

The solvents that can be used alone or in combination are aromatic solvents such as toluene, xylene, chlorine or pyridine, ethers such as THF, DME, MTBE or dioxane, chlorinated solvents such as dichloromethane, chloroform or 1,2-dichloroethane, esters such as ethyl acetate or butyl acetate, nitriles such as acetonitrile, ketones such as acetone or methyl isobutyl ketone, or amides such as DMF, DMAC or NMP.

Another embodiment consists in carrying out the operation in pyridine optionally containing toluene in the presence of para-toluenesulphonyl chloride at a temperature ranging from −20° C. to 20° C.

Another embodiment consists in carrying out the operation in toluene in the presence of a cosolvent such as pyridine in pyridine:toluene proportions ranging from 1:1 to 1:4, in the presence of para-toluenesulphonyl chloride at a temperature ranging from −30° C. to 20° C.

The amine diol derivative of formula (VI), in which R and R' are as defined above, is obtained by reduction from an imine diol, optionally not isolated, of formula (VII) in which R and R' represent, independently of one another, one or more hydrogen, halogen (Cl, F, Br, I), cyano or nitro radicals, linear or branched alkyl radicals containing from 1 to 6 carbon atoms, linear or branched alkoxy radicals containing from 1 to 6 carbon atoms, linear or branched alkyl carboxylate radicals, wherein the alkyl contains from 1 to 6 carbon atoms, or trifluoromethyl or trifluoromethoxy radicals.

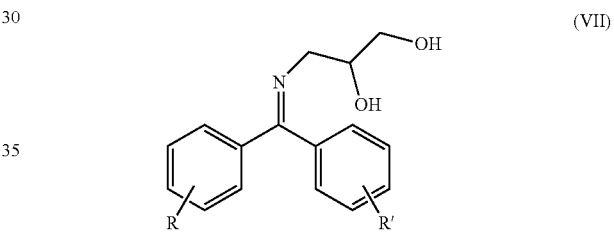

(VII)

The reducing agents used may be borohydrides, such as lithium borohydride, sodium borohydride, potassium borohydride, magnesium borohydride, calcium borohydride and zinc borohydride; borane complexes (borane-THF, borane-dimethyl sulphide, amine-boranes); or hydrogen gas in the presence of metal catalysts (palladium-on-charcoal, Raney nickel). The reducing agents are used in proportions ranging from 1 to 10 equivalents relative to the imine (VII). Depending on the compatibility with the reducing agents used, the solvents that can potentially be used are aromatic solvents such as toluene, xylene or chlorobenzene, ethers such as THF, DME, MTBE or dioxane, chlorinated solvents such as dichloromethane, chloroform or 1,2-dichloroethane, esters such as ethyl acetate or butyl acetate, alcohols such as methanol, ethanol, isopropanol or butanol, or water.

Another embodiment consists in carrying out the reduction in the presence of NaBH$_4$ in a water/ethanol mixture at 60° C.

The imine diol derivative of formula (VII) is synthesized from 3-amino-1,2-propanediol and a ketone of formula (VIII), in which R and R' represent, independently of one another, one or more hydrogen, halogen (Cl, F, Br, I), cyano or nitro radicals, linear or branched alkyl radicals containing from 1 to 6 carbon atoms, linear or branched alkoxy radicals containing from 1 to 6 carbon atoms, linear or branched alkyl carboxylate radicals, wherein the alkyl contains from 1 to 6 carbon atoms, or trifluoromethyl or trifluoromethoxy radicals.

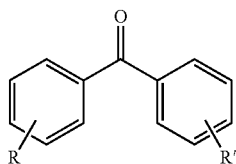

(VIII)

The imine diol of formula (VII) is formed by heating, in the presence or absence of solvent, at a temperature of between 0 and 150° C. and, optionally, in the presence of an acidic or basic catalyst or of a dehydrating agent. The dehydration of the medium may be optionally carried out by azeotropic distillation. The solvents that can potentially be used are aromatic solvents such as toluene, xylene, chlorobenzene or trifluoromethylbenzene, ethers such as THF, DME, MTBE or dioxane, chlorinated solvents such as dichloromethane, chloroform or 1,2-dichloroethane, esters such as ethyl acetate or butyl acetate, or alcohols such as methanol, ethanol, isopropanol or butanol. The acidic or basic catalyst is used in proportions ranging from 1 mol % to 100 mol % relative to the ketone.

The term "acidic catalyst" is intended to mean hydrochloric acid, hydrobromic acid, hydroiodic acid, tetrafluoroboric acid, hexafluorophosphinic acid, sulphuric acid, sulphonic acids such as methanesulphonic acid, p-toluenesulphonic acid, camphorsulphonic acid or trifluoromethanesulphonic acid, resin-supported sulphonic acids, carboxylic acids such as oxalic acid or formic acid, Lewis acids such as boron trifluoride etherate or rare-earth triflates.

The term "dehydrating agent" is intended to mean magnesium sulphate or sodium sulphate, or the use of a molecular sieve.

The term "base" is intended to mean hydrogen carbonates, carbonates, hydroxides or phosphates of lithium, sodium, potassium or caesium alkali metals. 3-aminopropane-1,2-diol is used in proportions ranging from 1 to 10 molar equivalents relative to the ketone.

Another embodiment consists in carrying out the operation in xylene at 140° C. by acid catalysis with 29% of para-toluenesulphonic acid.

In relation to document WO 01/64634, this new process provides improvements in terms of safety, and also a simplification of the steps for purifying and isolating the intermediate products or the final product, in particular by eliminating the use of reactants that are harmful to those who handle them, in order to make the process compatible with industrial production.

By way of example, the reaction scheme below illustrates in a nonlimiting manner the reactants used for each of the steps. In this scheme, R and R' represent chlorine atoms in the para position, R" represents a fluorine atom, and R'" and R1 represent a methyl group.

The reacting of (4,4')-dichlorobenzophenone and 3-aminopropane-1,2-diol under conventional conditions (acid catalysis with 29% of para-toluenesulphonic acid in a Dean-Stark apparatus) makes it possible to obtain the desired imine with a virtually quantitative yield. This product is not isolated, but is directly reduced through the action of NaBH$_4$ in an ethanol/water mixture at 60° C., so as to give the corresponding aminodiol with a yield of 90% for 2 steps.

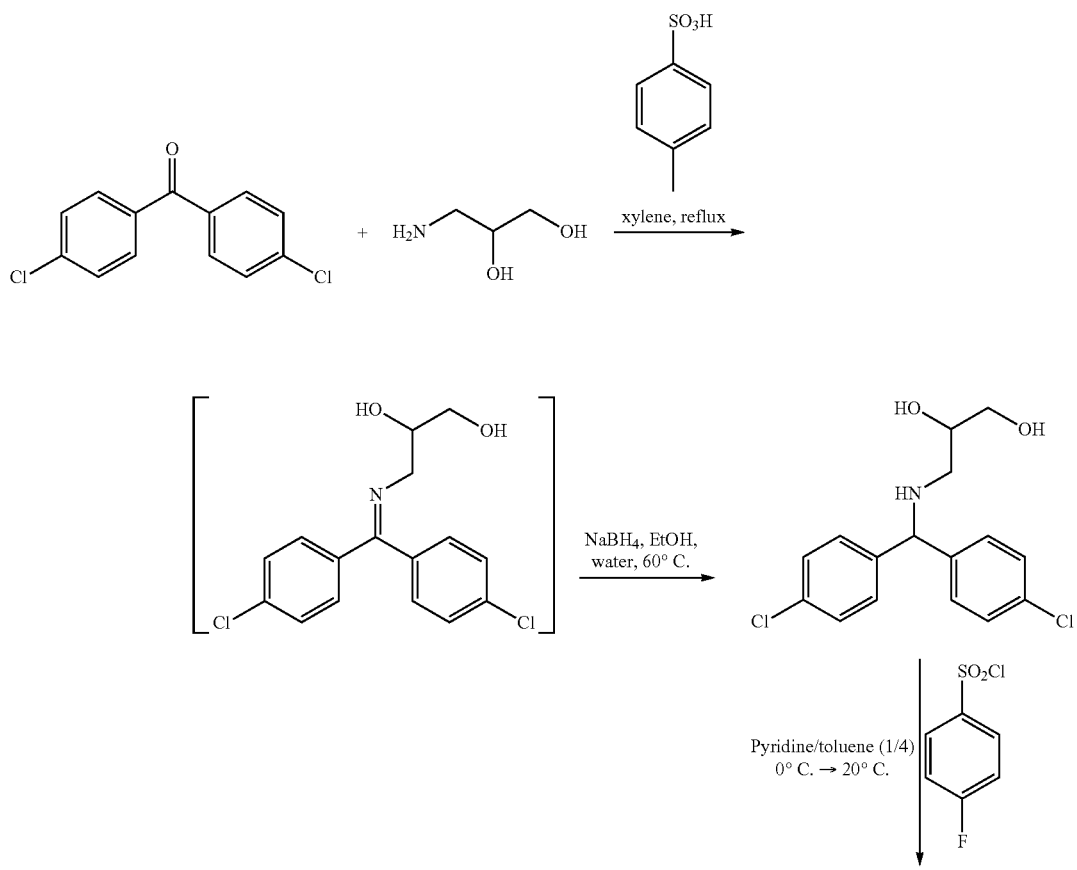

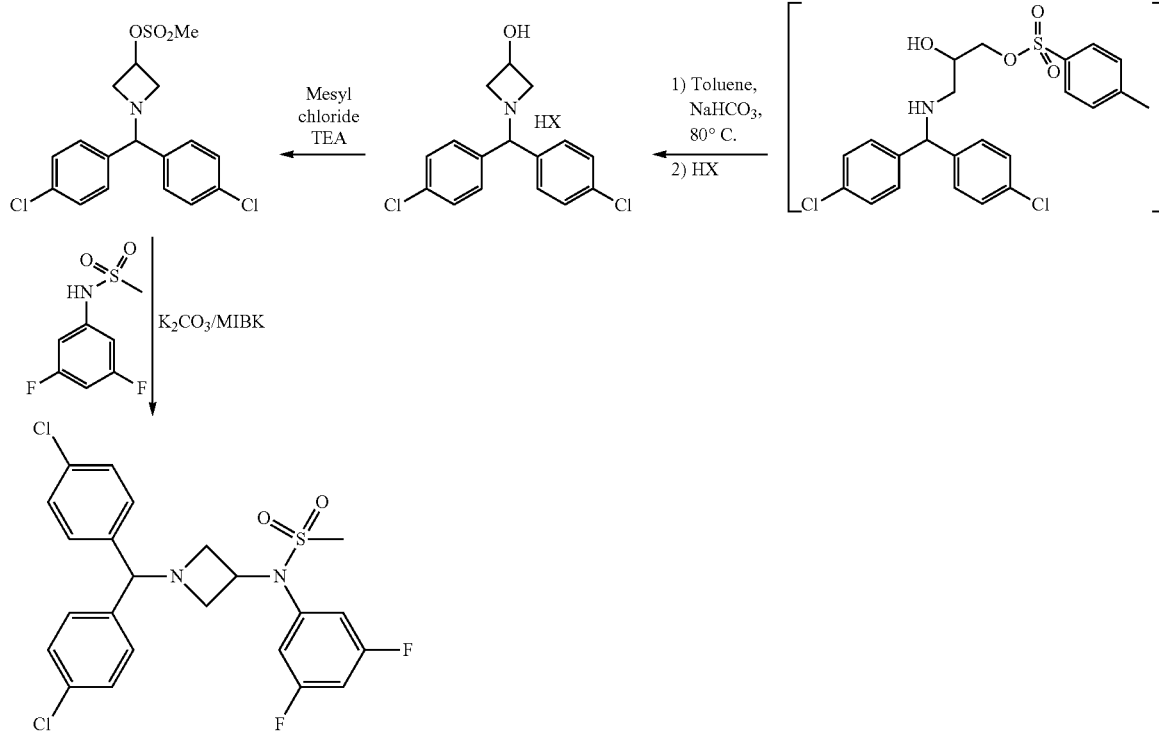

The aminodiol can be used in the following step without isolation or else can be isolated by crystallization from toluene or alternatively from a mixture of solvent with toluene. Among the solvents used, mention may be made of heptane, cyclohexane or methylcyclohexane.

This aminodiol, placed in the presence of para-toluenesulphonyl chloride in a pyridine/toluene mixture (from 1/1 to 1/4) first at −15° C., and then with the temperature allowed to rise to around 20° C., produces chemoselectively the monotosylate intermediate which is not isolated, but is directly cyclized in toluene under hot conditions (80° C.) in the presence of an inorganic base ($NaHCO_3$) for 4 hours.

After washing the organic phase with water, the product is purified by crystallization in hydrobromide form, so as to give 1-[bis(4-chlorophenyl)methyl]azetidin-3-ol hydrobromide with an overall yield of 63% for 4 steps.

Experimental section for the synthesis of 1-[bis(4-chlorophenyl)methyl]azetidin-3-ol hydrobromide, hydrochloride and tetrafluoroborate Steps 1 and 2

50 g of 4,4'-dichlorobenzophenone, 500 ml of xylene and a solution containing 54.5 g of 3-aminopropane-1,2-diol in 78.5 ml of ethanol are introduced, at a temperature of 20±2° C., into a 1.5-liter reactor equipped with a mechanical stirrer and a temperature probe, and placed under a nitrogen atmosphere. The ethanol is then removed by distillation by heating the solution thus obtained until the temperature at the top of the column reaches 140±2° C. The temperature of the reaction mass is then brought back to approximately 60±2° C., and then xylene is added so as to make the volume up to 500 ml. 10.97 g of para-toluenesulphonic acid are then added, and the reaction mass is then brought to a temperature of 140±2° C. while at the same time performing a constant-volume distillation for 13 hours. The reaction mass containing the 3-{[bis(4-chlorophenyl)methylene]amino}propane-1,2-diol is then concentrated to 3.25 volumes by distillation, and the temperature is then brought back to approximately 20±2° C. 250 ml of EtOH are then added, and the solution is then brought to 60±2° C. and then treated over approximately 60 minutes with 151 ml (1 mole per mole of product) of sodium borohydride solution (solution prepared extemporaneously from 8 g of sodium borohydride, 0.850 ml of caustic soda at 32% and 150 ml of demineralized water). It is understood that the 3-{[bis(4-chlorophenyl)methylene]amino}propane-1,2-diol may be optionally isolated after distillation and washing.

The solution obtained is kept stirring for 5 hours at 60±2° C. The reaction mass is then brought back to 20±2° C., and then treated with 387 ml of 2N hydrochloric acid over approximately 60 minutes at 20°/22° C. The reaction medium is then kept stirring for 2 hours. The reaction mass is then heated until it reaches 102° C., while at the same time distilling the solvent, and then brought back 60±2° C. 250 ml of xylene are added while at the same time continuing to cool the reaction medium. When the latter reaches 20±2° C., a sufficient amount of 2N sodium hydroxide to attain a pH value of between 8 and 9 is added (i.e. approximately 150 ml). The aqueous phase is separated by settling out and the organic phase is treated, with stirring, with 700 ml of demineralized water and then, over approximately 10 minutes, with a sufficient amount of 2N HCl to attain a pH value of between 1 and 2 (i.e. approximately 160 ml). The aqueous phase is separated by settling out and recovered, and then 400 ml of toluene are added and the mixture is then treated, with stirring, over approximately 10 minutes, with a sufficient amount of 2N sodium hydroxide to attain a pH value of between 10 and 11 (i.e. approximately 190 ml), while at the same time maintaining the temperature of the medium at approximately 20±2° C. After stirring for 30 minutes, the organic phase is separated by settling out and the aqueous phase is extracted with 100 ml of toluene. The organic phases are combined, washed with 200 ml of demineralized water and separated by settling out, and this operation is repeated a further 2 times. The toluenic phase thus obtained is then dehydrated by distillation at constant volume and at atmospheric pressure, of approximately 400 ml of toluene. 510 g of a toluenic solution of 3-{[bis(4-chlorophenyl)methyl]amino}propane-1,2-diol are thus obtained. This solution is used as it is in the next step.

The 3-{[bis(4-chlorophenyl)methyl]amino}propane-1,2-diol can be isolated by concentration of the toluenic solution to 2 volumes at 50° C., followed by the addition of 2 volumes of cyclomethylcyclohexane and cooling to 0° C. The product is spin-dried and washed with cyclomethylcyclohexane at 0° C., and oven-dried at 40° C. The yield is 86%.

Sum of impurities by HPLC: 0.4% m/m
Characteristics:
$^1$H NMR spectrum at 500 MHz, DMSO-$d_6$ referenced at 2.50 ppm at the temperature of 303 K: 2.33-2.40 (m, 2H), 2.51 (m, 1H), 3.32 (m, 2H), 3.58 (m, 1H), 4.44 (t, J=5.4 Hz, 1H), 4.58 (d, 4.9 Hz, 1H), 4.83 (s, 1H), 7.35 (d, J=8.3 Hz, 4H), 7.42 (d, J=8.3 Hz, 4H).

$^{13}$C NMR spectrum at 500 MHz, DMSO-$d_6$ referenced at 39.5 ppm at the temperature of 303 K: 51.0, 64.4, 64.9, 70.4, 128.3, 128.8, 131.2, 143.2.

Mass spectrum: m/z=325 Da)(M+°).
IR spectrum: KBr 3331; 2909; 2829; 1595; 1489; 1410; 1088; 1014; 813; 530; 504 cm$^{-1}$.

Steps 3 and 4

400 ml of a toluenic solution containing 44.17 g of 3-{[bis(4-chlorophenyl)methyl]amino}propane-1,2-diol, prepared as above, are placed in a 1.5-liter reactor equipped with a mechanical stirrer and a temperature probe, and under a nitrogen atmosphere, and then treated with 100 ml of pyridine. The solution thus obtained is cooled to −7±2° C., and then treated, portionwise, over approximately 5 minutes, with 27.2 g of para-toluenesulphonyl chloride. After the addition, the reaction medium is stirred for approximately 1 hour at −7±2° C., brought back up to approximately 20±2° C. over approximately 1 hour, and stirred at approximately 20±2° C. for approximately 18 hours. The reaction medium is then washed with 200 ml of demineralized water, the organic phase is separated by settling out, and then 100 ml of demineralized water are added and the pH of the reaction medium is brought to approximately 3 by adding 37% HCl. The reaction mass is stirred for approximately 10 minutes, and the organic phase is separated by settling out, recovered, and then washed with 100 ml of demineralized water. The reaction mass is stirred for approximately 10 minutes, and the organic phase is separated by settling out, recovered, and then washed with a sufficient amount of a 5% aqueous solution of NaHCO$_3$ to attain a pH value of greater than 5. The reaction mass is stirred for approximately 10 minutes, and the organic phase is separated by settling out, recovered, and then washed with 200 ml of demineralized water. The reaction mass is stirred for approximately 10 minutes, and the organic phase containing the 4-toluenesulphonic acid 3-{[bis(4-chlorophenyl)methyl]amino}-2-hydroxypropyl ester is separated by settling out, recovered, and then treated with 17.1 g of NaHCO$_3$. The reaction medium is heated to a temperature in the region of 79±2° C. and left at this temperature for approximately 4 hours. The temperature of the reaction mass is then brought back to approximately 20±2° C. and the mass is washed with three times 250 ml of demineralized water. Approximately 16 ml of a 48% solution of hydrobromic acid in water are then added, over 1 hour, to the toluenic solution thus obtained. The suspension is maintained at 20±2° C. for approximately 1 hour, and then the solid is filtered off, washed with three times 200 ml of toluene, then dried for 15 hours at 48±2° C. under a vacuum of approximately 20 mbar.

It is understood that the 4-toluenesulphonic acid 3-{[bis(4-chlorophenyl)methyl]amino}-2-hydroxypropyl ester can be isolated.

31.5 g of 1-[bis(4-chlorophenyl)methyl]azetidin-3-ol hydrobromide are thus obtained with a yield of 60%.

Characteristics
$^1$H NMR spectrum at 500 MHz, DMSO-$d_6$ referenced at 2.50 ppm at the temperature of 303 K: 3.80-4.30 (m, 4H), 4.50 (m, 0.7H), 4.63 (m, 0.3H), 5.99 (m, 1H), 6.24 (m, 1H), 7.50-7.65 (m, 8H), 10.07 (m, 0.7H), 11.41 (m, 0.3H).

Mass spectrum: m/z=307 Da)(M+°).
IR spectrum: KBr 3342; 2901; 2787; 2630; 2589; 2423; 1600; 1495; 1425; 1140; 1093; 1014; 815; 533; 504 cm$^{-1}$.

Another procedure consists in isolating the product in the hydrochloride form by running an aqueous solution of HCl into the toluenic solution of 1-[bis(4-chlorophenyl)methyl]azetidin-3-ol obtained as above.

The 1-[bis(4-chlorophenyl)methyl]azetidin-3-ol hydrochloride is thus obtained.

50 g of 3-{[bis(4-chlorophenyl)methyl]amino}propane-1,2-diol, prepared and isolated as above, are placed in a 1-liter reactor equipped with a mechanical stirrer and a temperature probe, and under a nitrogen pressure, and then treated with 150 ml of pyridine and 150 ml of toluene. The solution thus obtained is cooled to −15±2° C., and then treated portionwise, over approximately 5 minutes, with 73 g of para-toluenesulphonyl chloride in solution in 125 ml of pyridine and 125 ml of toluene. After the addition, the reaction medium is stirred for approximately 3 hours at −15±2° C., and brought back up to approximately 20±2° C. over approximately 1 hour, and then the reaction medium is washed with 225 ml of demineralized water, the organic phase is separated by settling out, and then 250 ml of dichloromethane are added. The organic phase is then washed by adding 410 ml of 37% HCl diluted to ½. The reaction mass is stirred for approximately 10 minutes, and the organic phase is separated by settling out, recovered, and then washed with 100 ml of demineralized water and then washed with a sufficient amount of a 5% aqueous solution of NaHCO$_3$ to attain a pH value of greater than 5. The organic phase containing the 4-toluenesulphonic acid 3-{[bis(4-chlorophenyl)methyl]amino}-2-hydroxypropyl ester is concentrated to 275 ml, then distilled at constant volume by addition of toluene so as to eliminate the dichloromethane, and then treated with 19.3 g of NaHCO$_3$. The reaction medium is heated to a temperature in the region of 79±2° C., and left at this temperature for approximately 4 hours. The temperature of the reaction mass is then brought back to approximately 20±2° C. and the mass is washed with 250 ml of demineralized water. 13.5 ml of a 12N solution of hydrochloric acid are then added, over approximately 1 hour, to the toluenic solution thus obtained. The suspension is maintained at 20±2° C. for approximately 5 hours, and then the solid is filtered off, washed with three times 100 ml of toluene, then dried for 15 hours at 48±2° C. under a vacuum of approximately 20 mbar.

43.1 g of 1-[bis(4-chlorophenyl)methyl]azetidin-3-ol hydrochloride are thus obtained with a yield of 81.7%.

Characteristics
$^1$H NMR spectrum at 400 MHz: (DMSO-$d_6$) referenced at 2.50 ppm at the temperature of 303 K: 3.70 to 4.20 (m, 4H); 4.47 (m, 0.8H); 4.68 (m, 0.2H); 5.97 (m, 1H); 6.34 (broad m, 1H); 7.50 (d, J=8.5 Hz, 4H); from 7.62 to 7.77 (m, 4H); 12.35 (broad m, 0.2H); 12.5 (broad m, 0.2H).

Mass spectrum: m/z=307 (M$^+$).

IR spectrum: KBr 3289; 2753; 2583; 2448; 1596; 1495; 1458; 1425; 1142; 1091; 1014; 815; 801 & 534 cm$^{-1}$.

Another procedure consists in isolating the product in tetrafluoroborate form by running, over approximately 1 hour, a 50% aqueous solution of HBF$_4$ into the toluenic solution of 1-[bis(4-chlorophenyl)methyl]azetidin-3-ol obtained as above. The suspension is maintained at 20±2° C. for approximately 1 hour, and the solid is then filtered off, washed with three times 200 ml of toluene, then dried for 15 hours at 48±2° C. under a vacuum of approximately 20 mbar.

The 1-[bis(4-chlorophenyl)methyl]azetidin-3-ol tetrafluoroborate is thus obtained.

$^1$H NMR spectrum at 400 MHz: (DMSO-d$_6$) referenced at 2.50 ppm at the temperature of 303 K: 3.85 (m, 2H); 4.25 (m, 2H); 4.50 (m, 0.6H); 4.58 (m, 0.4H); 5.87 (m, 1H); 6.20 (very broad m, 1H); 7.51 (d, J=9.0 Hz, 4H); 7.55 (d, J=9.0 Hz, 4H); 10.7 (broad m, 0.6H); 11.35 (broad m, 0.4H).

IR spectrum: KBr 3528; 3202; 2937; 2785; 2620; 1597; 1496; 1142; 1093; 1061; 1038; 1013; 803 & 530 cm$^{-1}$.

Mass spectrum: m/z=307 (M-H)$^+$.

Step 5

40 g (102 mmol) of 1-[bis(4-chlorophenyl)methyl]azetidin-3-ol hydrobromide, then 320 ml of methyl isobutyl ketone (MIBK) are introduced, at 20±2° C., into a 1.5-liter reactor equipped with a dropping funnel, a mechanical stirrer and a temperature probe, and placed under a nitrogen atmosphere. The mixture is stirred for 30 minutes and then 44 ml of triethylamine are added, over 20 minutes, while at the same time reducing the temperature to −5° C. The funnel is rinsed with 40 ml of methyl isobutyl ketone. The medium is cooled to −10°±2° C. and methanesulphonyl chloride (12 ml, 153 mmol) is added dropwise over approximately 30 minutes while at the same time maintaining the temperature at −10°±2° C. The white suspension is kept stirring for 1 hour at −12°±2° C. The whole mixture is brought back to 20°±2° C., and then stirred for 1 hour. 160 ml of a solution containing 50 g/l of sodium hydrogen carbonate are added over approximately 10 minutes. The organic phase becomes clear and the aqueous phase is cloudy. Stirring is maintained for 30 minutes, and then the whole is separated by settling out and the organic phase is then washed with 2×80 ml of a solution containing 50 g/l of sodium hydrogen carbonate. 2 clear phases are obtained. After elimination of the aqueous phase, 400 ml of a solution of azetidinol mesylate in MIBK are recovered, which solution is used as it is for the next reaction.

Step 6

21.37 g (105 mmol) of N-(3,5-difluorophenyl)methylsulphonamide and then 42.4 g of anhydrous potassium carbonate are added to the solution of 400 ml of methyl isobutyl ketone containing 1-[bis(4-chlorophenyl)methyl]azetidin-3-yl methyl sulphonate. The whole mixture is brought to reflux at a temperature of 105° C. and stirred at this temperature for 4 hours. The temperature is then brought back to 25° C. over 30 minutes and 200 ml of methyl isobutyl ketone followed by 200 ml of water are added. The mixture is stirred for 15 minutes. The medium is separated by settling out and the organic phase is washed with 200 ml of water for 15 minutes. The whole is again left to separate by settling out.

The organic phase is then concentrated by distillation of approximately 500 ml of MIBK with stirring, under a vacuum of approximately 23 mbar and at a temperature of approximately 24° C.±2° C. The N-{1-[bis(4-chlorophenyl)methyl] azetidin-3-yl}-N-(3,5-difluorophenyl)methylsulphonamide is precipitated by adding to the medium 480 ml of isopropanol a 25° C.±2° C. The temperature is reduced to −3° C. over approximately 15 minutes and stirring is carried out at this temperature for 14 hours.

The suspension is subsequently filtered over sintered glass. The reactor is washed twice with 80 ml of isopropanol at 3° C., and the cake thus obtained is then washed using the recovered fractions of isopropanol.

A mass before drying of 53.94 g is obtained. After drying for 24 hours under a vacuum of approximately 40 mbar, and at a temperature of 40° C., 39.34 g of N-{1-[bis(4-chlorophenyl)-methyl]azetidin-3-yl}-N-(3,5-difluorophenyl)methylsulphonamide are obtained, i.e. a yield of 77.4%.

The conditions described in the above example (steps 5 and 6) were applied under similar conditions starting with 1-[bis (4-chlorophenyl)methyl]azetidin-3-ol hydrochloride, and resulted in N-{1-[bis(4-chlorophenyl)methyl]azetidin-3-yl}-N-(3,5-difluorophenyl)methylsulphonamide being obtained with a yield of 76.7%

The invention claimed is:

1. A process for synthesizing azetidine derivatives represented by formula (I), comprising the steps of:

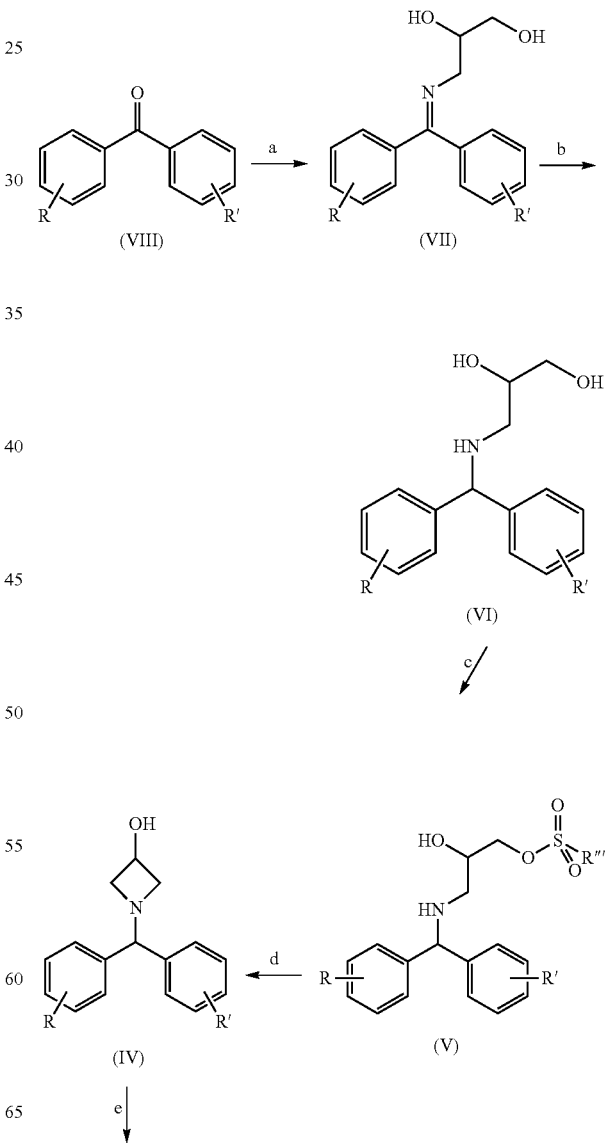

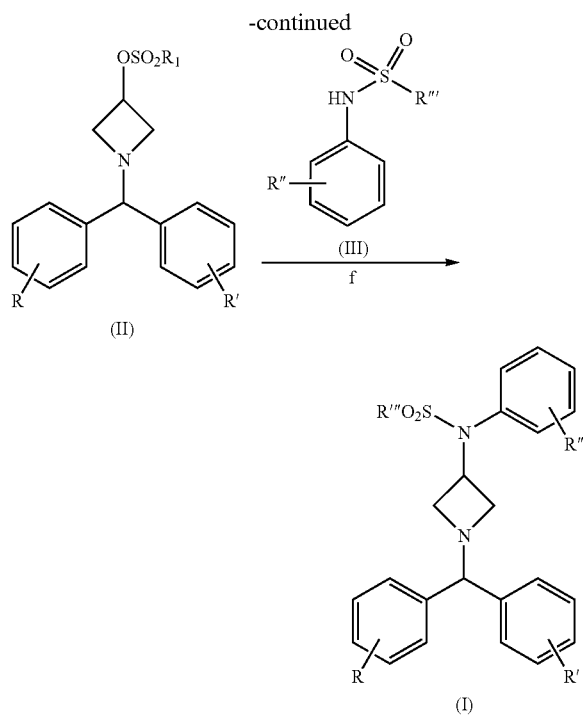

a) a ketone of formula (VIII) is condensed with 3-amino-1,2-propanediol, in the presence or absence of a solvent, in the presence or absence of an acidic or a basic catalyst, at a temperature of between 0° C. and 150° C. so as to form an imine diol of formula (VII);
b) the imine diol of formula (VII) which is optionally not isolated, is reduced with a borohydride or hydrogen gas, in the presence of a metal catalyst in a solvent so as to form an amine diol of formula (VI);
c) the amine diol of formula (VI) which is optionally not isolated, is activated with a sulphonylating agent in the presence of a base, in a solvent and optionally a cosolvent at a temperature ranging from −78° C. to 40° C. so as to form a sulphonic ester of formula (V), which is optionally not isolated;
d) the sulphonic ester of formula (V) is cyclized by heating in a solvent in the presence or absence of a base, between 0° C. and 130° C., so as to form an azetidinol of formula (IV), which is optionally isolated in the form of a salt;
e) the azetidinol of formula (IV) or the salt thereof, is converted to a sulphonate of formula (II) through the action of a sulphonylating agent in the presence of a base, in a solvent, at a temperature of between −78° and +40° C.;
f) the sulphonate of formula (II) is condensed with a sulphonamide of formula (III) in the presence of a base, in the same solvent as that used in step e), so as to form a compound of formula (I);
wherein in formulae (I), (II), (III), (IV), (V), (VI), (VII) and (VIII), R, R' and R" represent, one or more moieties independently selected from the group consisting of hydrogen, halogen, cyano or nitro radicals, linear or branched alkyl radicals containing from 1 to 6 carbon atoms, linear or branched alkoxy radicals containing from 1 to 6 carbon atoms, linear or branched alkyl carboxylate radicals wherein the alkyl contains from 1 to 6 carbon atoms, and trifluoromethyl or trifluoromethoxy radicals; R'" represents a linear or branched alkyl or perfluoroalkyl group containing from 1 to 6 carbon atoms or an aryl group optionally substituted with one or more R" radicals; and R1 represents a methyl group, $CF_3$ group, $C_4F_9$ group, $C_8F_{17}$ group or a phenyl group optionally substituted with a methyl, halo or nitro group.

2. The process according to claim 1, wherein, in step a), the solvent is xylene and the catalyst is para-toluenesulphonic acid.

3. The process according to claim 1, wherein in step d), the solvent is toluene or xylene, the base is $NaHCO_3$ or $Na_2CO_3$, and the temperature ranges from 0 to 130° C.

4. The process according to claim 3, in which the temperature ranges from 40 to 110° C.

5. The process according to claim 1, wherein in step c), the solvent is pyridine optionally containing toluene and the sulphonylating agent is para-toluenesulphonyl chloride, at a temperature ranging from −78° C. to +40° C.

6. The process according to claim 5, in which the temperature range is from −30° C. to +20° C.

7. The process according to claim 6, wherein the solvent and the co-solvent are toluene and pyridine in proportions of 4:1.

8. The process according to claim 1, wherein in step b), the borohydride is $NaBH_4$ and the solvent is a water/ethanol mixture at 60° C.

9. The process according to claim 1, wherein the product derived from step d) is 1-[bis(4-chlorophenyl)methyl]azetidin-3-ol or the salt thereof.

10. The process according to claim 9, in which the salt product is 1-[bis(4-chlorophenyl)methyl]azetidin-3-ol hydrobromide.

11. The process according to claim 9, in which the salt product is 1-[bis(4-chlorophenyl)methyl]azetidin-3-ol hydrochloride.

12. The process according to claim 9, in which the salt product is 1-[bis(4-chlorophenyl)methyl]azetidin-3-ol tetrafluoroborate.

13. The process according to claim 1, wherein the product represented by Formula (VII) is 3-{[bis(4-chlorophenyl)methylene]amino}propane-1,2-diol.

14. The process according to claim 1, wherein the product represented by Formula (VI) is 3-{[bis(4-chlorophenyl)methyl]amino}propane-1,2-diol.

15. The process according to claim 1, wherein the product represented by Formula (V) is 4-toluenesulphonic acid 3-{[bis(4-chlorophenyl)methyl]amino}-2-hydroxypropyl ester.

16. The process according to claim 1, in which Formula (VII) is 3-{[bis(4-chlorophenyl)methylene]amino}propane-1,2-diol; Formula (VI) is 3-{[bis(4-chlorophenyl)methyl]amino}propane-1,2-diol; and Formula (V) is 4-toluenesulphonicacid-3-{[bis(4-chlorophenyl)methyl]amino}-2-hydroxypropyl ester.

17. The process according to claim 1, in which Formula (IV) is 1-[bis(4-chlorophenyl)methyl]azetidin-3-ol hydrochloride or 1-[bis(4-chlorophenyl)methyl]azetidin-3-ol tetrafluoroborate.

18. The process according to claim 1, wherein when the value for R, R' or R" is halogen, said halogen is one or more of Cl, F, Br or I.

19. The process according to claim 1, in which Formula (I) is N-{1-[bis(4-chlorophenyl)-methyl]azetidin-3-yl}-N-(3,5-difluorophenyl)methylsulphonamide.

* * * * *